United States Patent [19]

McCandliss et al.

[11] Patent Number: 4,536,207

[45] Date of Patent: Aug. 20, 1985

[54] NEMATOCIDALLY ACTIVE CHITIN-PROTEIN COMPLEX

[75] Inventors: Russell J. McCandliss, Germantown, Md.; Barbara J. Eastwood, Round Hill, Va.; Robert A. Milch, Baltimore, Md.

[73] Assignee: IGI Biotechnology, Inc., Columbia, Md.

[21] Appl. No.: 517,312

[22] Filed: Jul. 26, 1983

[51] Int. Cl.$^3$ .................. C07G 7/00; E05B 65/48; E05B 65/46

[52] U.S. Cl. .................. 71/88; 260/112 R; 536/20; 71/3; 71/4

[58] Field of Search .............. 260/112 R; 536/20; 71/3, 4, 88

[56] References Cited

U.S. PATENT DOCUMENTS

| | | | |
|---|---|---|---|
| 2,040,879 | 5/1936 | Rigby | 536/20 |
| 3,862,122 | 1/1975 | Peniston et al. | 260/112 R X |
| 4,195,175 | 3/1980 | Peniston et al. | 536/20 |
| 4,199,496 | 4/1980 | Peniston et al. | 260/112 P |
| 4,373,096 | 2/1983 | Koshugi | 260/112 R X |
| 4,390,468 | 6/1983 | Sasaki et al. | 260/112 R |

OTHER PUBLICATIONS

Max LaFon, "Nouvelles Recherches Biochimiques et Physiologiques sur le Squellete Tegumentaire des Crustaces", Bull. Inst. Oceanographique, 45, No. 939, Oct. 5, 1948, pp. 1–28.
Webster's 7th Collegiate Dictionary, p. 252.

*Primary Examiner*—Howard E. Schain
*Attorney, Agent, or Firm*—Haight & Associates

[57] ABSTRACT

A chitin-protein complex is prepared from chitin-containing biological waste material such as crustacean shells. The complex is different from both chitin and chitosan, and has useful nematostatic and nematocidal activity for agricultural and horticultural applications by admixing nematocidally effective amounts with a plant growth medium. The complex also provides a source of nitrogen in slow-release form, making it particularly suitable for combination with fertilizers, soil conditioners, etc.

20 Claims, 11 Drawing Figures

ELECTRICAL PROPERTIES OF CHITIN, CHITOSAN, AND CHITIN-PROTEIN COMPLEX

EXAMPLE OF LIVING NEMATODES

EXAMPLE OF LIVING NEMATODES

CHITIN-PROTEIN COMPLEX TREATED NEMATODES
(IMMOBILE, DEAD)
NOTE VACUOLIZATION

DEAD CHITIN-PROTEIN COMPLEX TREATED NEMATODES

NEMATODES STAINED WITH THE AVITAL STAIN, BRILLIANT GREEN

NEMATOCIDALLY ACTIVE CHITIN-PROTEIN COMPLEX

DESCRIPTION OF THE INVENTION

1. Technical Field of the Invention

This invention relates to a process for converting shellfish wastes into useful products and for avoiding costly traditional methods for disposing of low economic value waste products of the shellfish processing industry. More particularly, the invention relates to methods for the isolation and recovery of a naturally occuring chitin-protein complex from the tough polymer matrix of crustacean exoskeletons and to methods for using these polymeric compositions for inhibiting the growth of plant-parasitic and other nematodes of interest in horticulture and agriculture.

2. Background Art

Nematodes (nema—thread; oides—resembling), or unsegmented roundworms with elongated, fusiform, or saclike bodies covered with cuticle, which belong to the phylum Nemathelminthes, are virtually ubiquitous in nature, inhabitating soil, water and plants, and are importantly involved in a wide range of animal and plant parasitic diseases.

While there are some significant problems related to nematodiasis in animals, it seems likely that major interest will continue to focus on nematodes which parasitize the roots, stems, leaves and seeds of plants and are major contributing factors to crop losses and to serious economic losses to agricultural productivity on a worldwide basis. These include, by way of example, root-knot (*Meloidogyne spp.*), root-lesion (*Pratylenchus spp.*), spiral (*Heliocotylenchus spp.*), and burrowing nematode (*Radopholus similis*), which is highly destructive of citrus crops and more than 200 other species of plants. Damaging levels of stunt (*Tylenchorynchus spp.*), reniform (*Rotylenchulus spp.*) and filiar (*Amphelenchoides spp.*) nematodes are also found in foliage ornamentals. Ring (*Macroposthonia xenoplax*) and dagger (*Xiphinema spp.*) nematodes infect peach orchards, and soybeans are often seriously infested with both the soybean cyst nematode (*Heterodera glycines*) and root-knot (*Meloidogyne spp.*).

In the Unites States alone, approximately two million acres of agricultural land are treated each year by prophylactic and quarantine measures, chemical control, soil fumigation, hot-water treatment, and resistance-based selection methods in order to control nematodes. This includes land used to grow nonfood crops (e.g., cotton and tobacco), field crops (e.g., corn and wheat), orchard crops (e.g., apples, citrus and nuts), vegetables (e.g., potatoes) and a wide range of ornamentals. Almonds, apples, asparagus, citrus (including oranges, grapefruit, lemons and limes), cotton, grapes, melons, peaches, peanuts, pineapples, soybeans and strawberries, among other edible plant foods, and essentially all vegetables are susceptible to nematode infestation, as are home gardens and lawns, commercial turf, ornamentals and most other plants. Furthermore, large areas of otherwise arable agricultural lands (i.e., croplands, pasturelands, forest lands and lands in other agricultural use) may lie fallow or unused owing directly or indirectly to overwhelming or uncontrolled nematode infestations.

Plant-protection methods for nematode control, including crop rotation, soil-treatment and fertilization practices, and "green manuring" with sweet clover or mustard, as well as physical methods of soil treatment, such as steaming of soil and hot-water treatment of planting stocks, have generally met with only limited success. Chemical methods, on the other hand, employing a range of systemic pesticides, have been reasonably successful, particularly in horticultural practice, despite the fact that nematodes tend to be resistant to many of the pesticidal agents which have been marketed for application either in a gaseous form (fumigation) or dispersed in soil in liquid or solid forms; (see, for example, A. C. Tarjan and P. C. Cheo, "The Nematode Screening Program of the University of Rhode Island," Contribution 887, Agricultural Experiment Station, Kingston, R.I., March, 1956).

Currently, only some 25 nematocidal chemicals are registered with the U.S. Environmental Protection Agency (EPA) for use on important food, feed and fiber crops. Most nematocides now available in commercial markets are, moreover, quite toxic to both man and animals, in large part being organic thiophosphate (phosphorothioate and phosphorodithioate) compounds and cholinesterase inhibitors. Many of them are also phytotoxic. Because of their adverse effects on the environment, several nematocides which are currently marketed are subject to review which may result in cancellation of registration. Thus, issues of safety and efficacy as well as of agricultural economics are critical considerations in the control of plant-parasitic nematodes. A clear and present commercial need exists for nematostatic or nematocidal materials, preferably biological control agents, which are non-toxic for plants, animals and man.

Despite the widespread presence in almost all soils, especially those with a high content of decomposing organic matter, protozoa, bacteria, predatory nematodes, and fungi which can in theory act as biological control agents against plant-parasitic nematodes, biological control programs have not been instituted on a large-scale anywhere in the world; see, for example, K. F. Baker and R. J. Cook, *Biological Control of Plant Pathogens*, W. H. Freeman and Company, San Francisco, Calif., 1974 and H. Decker, *Plant Nematodes and Their Control (Phytonematology)*, published for the U.S. Department of Agriculture and the National Science Foundation, Washington, D.C. by Amerind Publishing Co., Ltd., New Delhi, India, 1981.

Few efforts have been made to analyze in a systematic and orderly manner the biological effects of deliberate introduction into soils of relatively large amounts of the type of non-toxic organic wastes which may accumulate and cause serious environmental and economic consequences in specific geographic regions, such as the Chesapeake Bay (e.g., R. A. A. Muzzarelli and E. R. Pariser, Eds., *Proceedings of the First International Conference on Chitin/Chitosan*, MIT Sea Grant Report, MITSG 78-7, Cambridge, Mass., 1978; B. L. Averbach, "Chitin/Chitosan Production for Utilization of Shellfish Wastes," pp. 285–300, in W. S. Otwell, Ed. *Seafood Waste Management in the 1980's: Conference Proceedings,* Florida Sea Grant Program, Report No. 40, February, 1981; T. P. Cathcart et al., "Composting Blue Crab Processing Plant Solid Waste". Annual Report, Department of Agriculture Engineering, University of Maryland, College Park, Md., Dec. 31, 1981; and T. M. Cook, "Development of a Fermentation Process to Use Wastes from the Chesapeake Bay Industry". Report F-16-81-005, Department of Microbiology, University of Maryland, College Park, Md. March 1982).

Laboratory studies undertaken by Brown et al. have, however, shown that dried and powdered seafood wastes—including commercially available chitin and chitosan, alkali-treated (3.5% NaOH for 24 hours) and non-treated shrimp shell wastes—when utilized as a soil amendment cause a statistically significant decrease in root-knot infestation and a statistically significant increase in the number of chitinolytic actinomycetes in both tomato and ornamental plants (see, for example, L. R. Brown et al.: "The Use of Chitinous Seafood Wastes for The Control of Parasitic Plant Nematodes", MMRC Project No. GR-76-004 and CO-76-020, Mississippi Marine Resources Chronical, Long Beach, Miss., October, 1977 and "The Use of Chitinous Seafood Wastes for the Control of Plant Parasitic Nematodes", BMR Project No. GR-ST-78-003 and GR-ST-78-004, Bureau of Marine Resources, Mississippi Department of Wildlife Conservation, Long Beach, Miss., September, 1979).

Problems associated with the accumulation of crab-shell wastes in the Chesapeake Bay region (or, by way of further example, shrimp shell wastes around the Gulf of Mexico) and often conflicting observations on the role and effect of chitin and chitosan materials isolated from these wastes prompted the laboratory investigations which led to the product and process of the present invention. Relevant observations include published reports that: (a) the addition to soils of crop residues and other carbonaceous materials appears to suppress both nematodes and certain fungi in soil populations (e.g. M. B. Linford et at., "Reduction of Soil Populations of the Root-Rot Nematode During Decomposition of Organic Matter", *Soil Sci.*, 45: 127, 1938, and C. B. Davey and G. C. Papavizas, "Effect of Organic Soil Amendments of the Rhizoctonia Disease of Snap Beans", *Agron, J.*, 51: 493, 1959); (b) small additions of commercially available chitin, but not of chitosan or N-acetylglucosamine, seem able to stimulate chitinase-producing microorganisms in the soil and to reduce the severity of root-rot of beans caused by Fusarium (e.g., R. Mitchell and M. Alexander, "The Mycolytic Phenomenon and Biological Control of Fusarium in Soil", *Nature*, 190: 1961, and R. Mitchell and M. Alexander, "Chitin and the Biological Control of Fusarium Diseases", *Plant Disease Reporter*, 45: 487, July 15, 1961; (c) chitosan, but not chitin, inhibits the growth of many fungi, including plant and animal pathogens, in culture media (e.g., C. R. Allan and L. A. Hadwiger, "The Fungicidal Effect of Chitosan on Fungi of Varying Cell Wall Composition." *Exp. Mycology*, 3:285, 1979); and (d) commercial preparations of chitosan have little or no effect in reducing either the chemical or biological oxygen demand of wastewater effluents from crab processing operations (e.g., F. W. Wheaton et. al., "Wastewater Characterization and Treatment System Development for a Blue Crab Processing Plant." WRRC Technical Report No. 65, University of Maryland, College Park, Md., April 1981.)

Several attempts at developing useful methods for dealing with chitin disposal have also been described in the patent literature (e.g., see Austin, U.S. Pat. Nos. 3,879,377; 3,892,731 and 4,286,087 Balassa, U.S. Pat. Nos. 3,903,268; 3,911,116 and 3,914,413, Dunn, U.S. Pat. No. 3,847,897; Casey, U.S. Pat. No. 4,059,097; Muralidhara, U.S. Pat. No. 4,293,098; and Muzzarelli, U.S. Pat. No. 4,282,351), the contents of which are incorporated by reference herein. Various techniques are also known in the art for recovering chitosan from chitin (e.g., Rigby, U.S. Pat. No. 2,040,879, Penniston, U.S. Pat. Nos. 3,862,122 and 4,195,175), the contents of which are incorporated by reference herein.

DISCLOSURE OF THE INVENTION

It is a general object of this invention to provide improved and economically advantageous methods for disposing of otherwise low economic value wastes remaining after commercial shellfish processing operations.

Another object of this invention is to provide a process for converting chitin-containing biomass waste materials into industrially useful compositions, preferably into forms and compositions of matter which have use in agriculture, horticulture and animal husbandry.

A further object of the invention is to provide an improved and inexpensive means for obtaining commercial quantities of materials from naturally occurring chitin-containing biomass which can be demonstrated to induce nematostatic and nematocidal activity in culture media and in soil samples.

A more particular object of the invention is to provide a newly isolated chitin-protein complex which can be obtained from naturally occurring sources and has demonstrable nematocidal activity for prototypical nematode species without evidence of a direct toxic effect on nematodes.

Upon study of the specification and appended claims, further objects, features and advantages of this invention will become more fully apparent to those skilled in the art to which this invention applies.

The present invention involves the discovery that a nematocidally active chitin-protein complex can be easily and economically prepared by mild acid hydrolysis of crustacean shell wastes, with or without recovery of carbon dioxide and other volatile gases produced during demineralization and partial protein degradation. The resulting chitin-protein complex induces nematocidal activity in nematode cultures in vitro, characterized by microscopic evidence of premature senescence and gas vacuole formation accompanied by loss of motility and death. Dead and dying nematodes, in sharp contrast to viable and highly motile forms, take up Brilliant Green and Brilliant Cresyl Blue stains.

Because of the nematocidal activity that is induced by the chitin-protein complex described herein and the ease and low cost of its manufacture in commercial quantities, addition of this material to agricultural and horticultural soils for the purpose of control of plant-pathogenic nematodes provides an economically and environmentally attractive means for the use of otherwise low value shellfish wastes and a means for reducing food, fiber and economic losses due to nematode infestations. Incorporation of these materials into animal feeds also offers a potential means for control of intestinal tract nematodiasis and a rich source of dietary protein.

BRIEF DESCRIPTION OF THE DRAWINGS

The present invention will become more fully apparent to those skilled in the art from the following description, taken in conjunction with the annexed drawings, wherein.

BEST MODE FOR CARRYING OUT THE INVENTION

The chitin-protein complex of this invention can be prepared from any suitable chitin-containing biomass raw material. Such materials include but are not limited to invertebrate marine organisms having visible shells. Examples of such organisms are arthropods, including crustaceans, mollusks, marine benthic organisms and krill fish. Preferred shellfish waste is that obtained from crustaceans such as crabs, lobsters, crayfish, shrimp and prawns. Cell walls and filamentous masses of true fungi, including Phycomycetes and Ascomycetes species (which can be digested by one or more of the over 30 enzymes, including chitinase, glucanase and mannanase, contained in the digestive juice of the snail *Helix pomatia* or produced by certain bacteria, such as some soil scavenging Pseudomonas species which have been isolated from soils) contain chitin but do not ordinarily provide a suitable raw material or feedstock for a commercial process because of the amounts of these materials presently available. Because it is the presently preferred embodiment, the preparation of the chitin-protein polymer complex obtained from the shells of blue crabs (*Callinectes sapidus*) harvested from the Chesapeake Bay will be described in detail.

In conventional blue crab processing operations (see, for example, pages 206–207 in E. J. Middlebrooks, *Industrial Pollution Control, Volume 1; Agro-Industries*, John Wiley and Sons, New York, 1979) crabs are dredged from the mud, caught in baited traps or lines or scraped from grassy shores during the molt. Baited pots are used to trap Dungeness, Tanner and King crabs which are then stored in circulating seawater in shipboard and/or in landbased tanks prior to processing, usually in dry butchering. Blue crabs are transported live to the processing plant and are unloaded into trolleys for immediate steam cooking at 121° C. for 10–20 minutes. The cooked crabs are then stored overnight in a cooling locker after which the claws are removed and saved for later processing. After removal of the carapace and claws, the claws and sometimes the bodies of the crabs are either run through a mechanical picker or picked manually to separate residual meat from the shell. Crab processing waste is generally discharged to a waterway or a municipal sewer, hauled to a sanitary landfill or otherwise rendered, frequently by drying and shredding for eventual use as a feed meal, especially for chickens (see, for example, P. R. Austin et al., "Lactose-Rich Animal Feed Formulations and Methods of Feeding Animals". U.S. Pat. No. 4,320,150, to W. P. Uri Yrains, Jr. and T. M. Miller, and "Prices based on Nutritional Worth, Crab Meals and Crab Meal-Phosphoric Acid Supplements in the Diets of Monogastric Animals", Final Report (F15-81-005) to Department of Natural Resources, Maryland Tidewater Administration (March, 1982).

Figure 1:
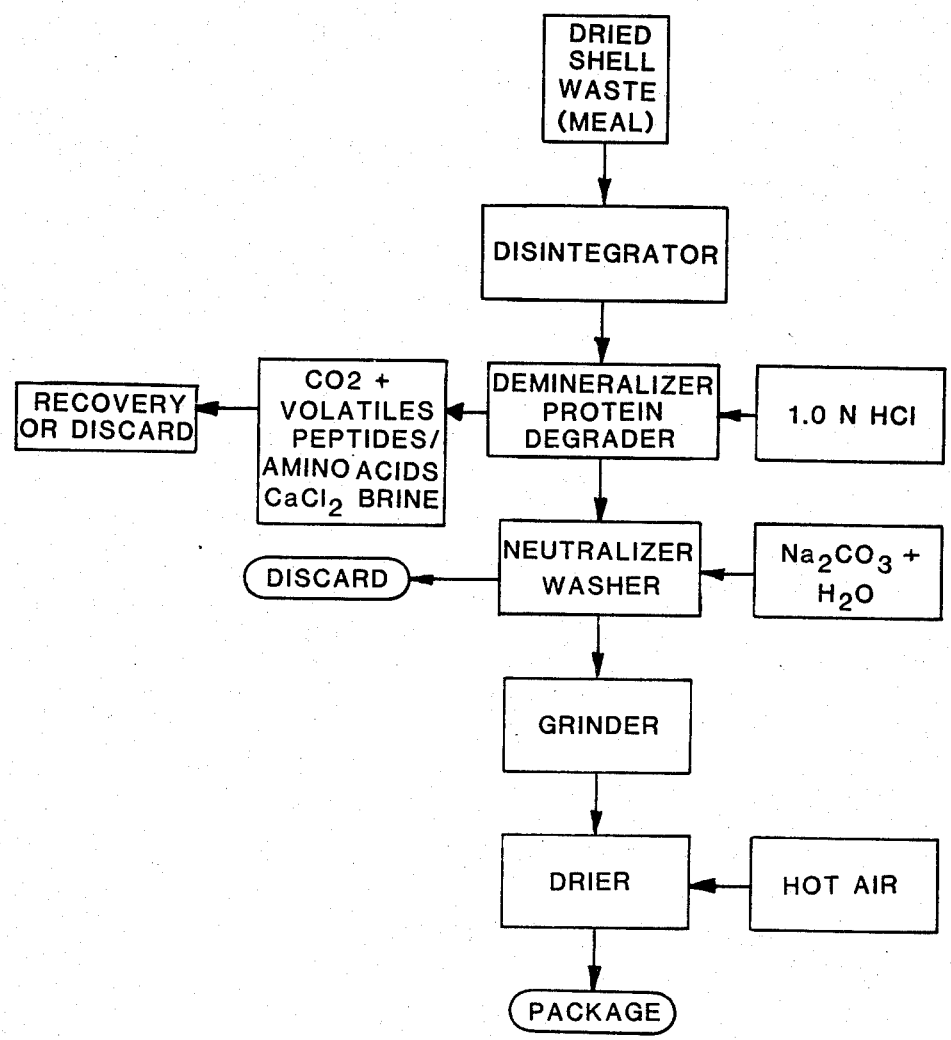
FIG. 1 illustrates the process for producing the chitin-protein complex of this invention and identifies by-products which can be recovered.
Figure 2A:
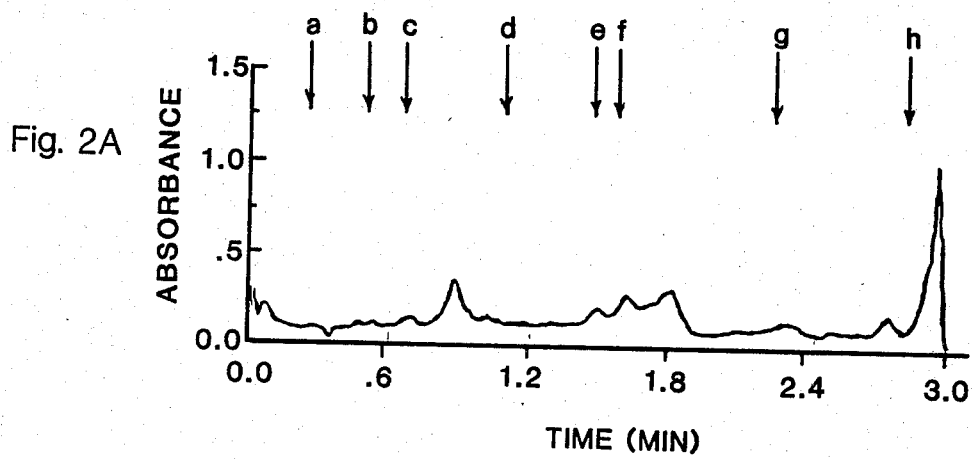
FIG. 2 illustrates the subunit composition of the protein component of crabshell waste treated according to the process described in Example 2.
Figure 2B:
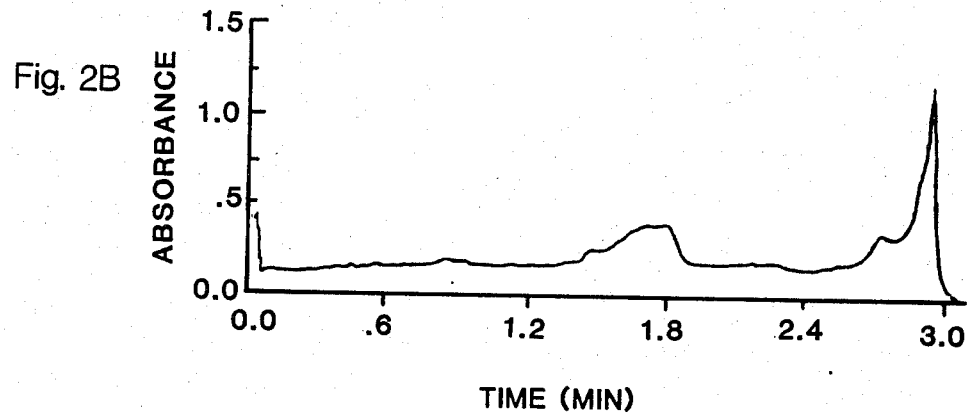
Figure 2C:
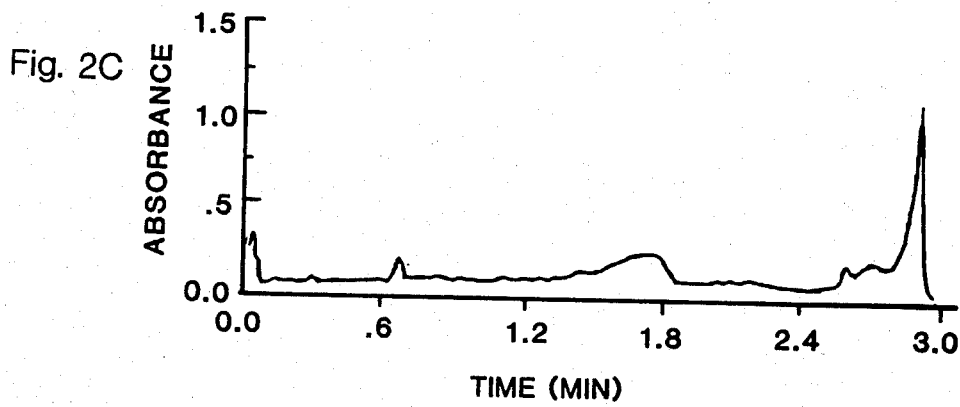
Figure 2D:
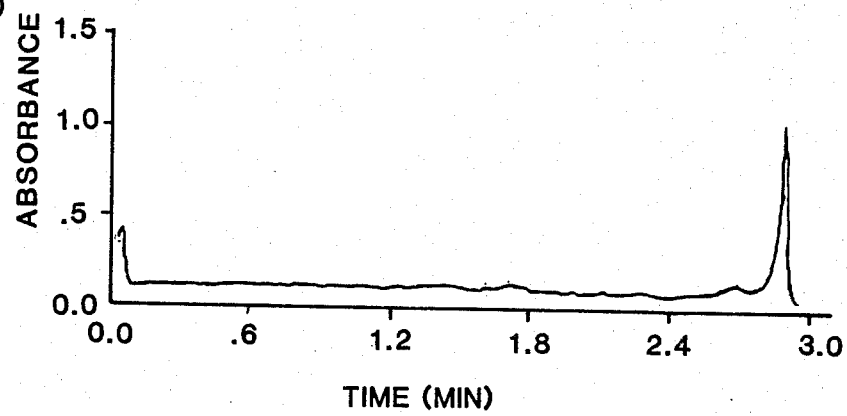
Figure 2E:
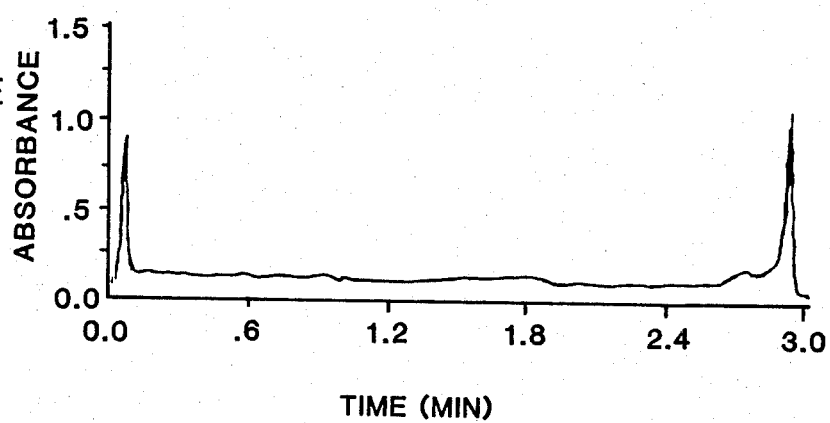

The presently preferred starting or raw material for the herein disclosed invention (FIG. 1) is such crab processing waste material which has been oven-dried and shredded to a small particle size. To reduce costs of raw materials, the drying step can be omitted. The exact particle size which is used affects the rate but not the nature of the process. Composition of the crabmeal raw material varies both with the season and with the thoroughness with which meat is removed from the shells, but the raw material generally contains protein (40–50%), calcium carbonate and small amounts of other mineral salts (about 50%), and chitin (about 10%).

Dried and shredded shell wastes are milled or ground to a desired particle size and either used directly or washed with hot or cold water to remove contaminants which may have developed during transportation, if required, to a processing facility. Shell fragments are then demineralized in a stirred tank reactor using a dilute mineral acid, such as 1.0N HCl, for a period of 30–60 minutes, generally under ambient temperature and pressure. Acids such as sulfuric and phosphoric are not suitable since they result in insoluble calcium salts which interfere with recovery of the product. The demineralization reaction, which is accompanied by significant modification of the protein component of the crab shells (FIG. 2) and by the release of carbon dioxide gas containing detectable amounts of the "fishy" odors characteristic of alkyl amines, can be followed by titration or by observation of gas release.

Figure 3:
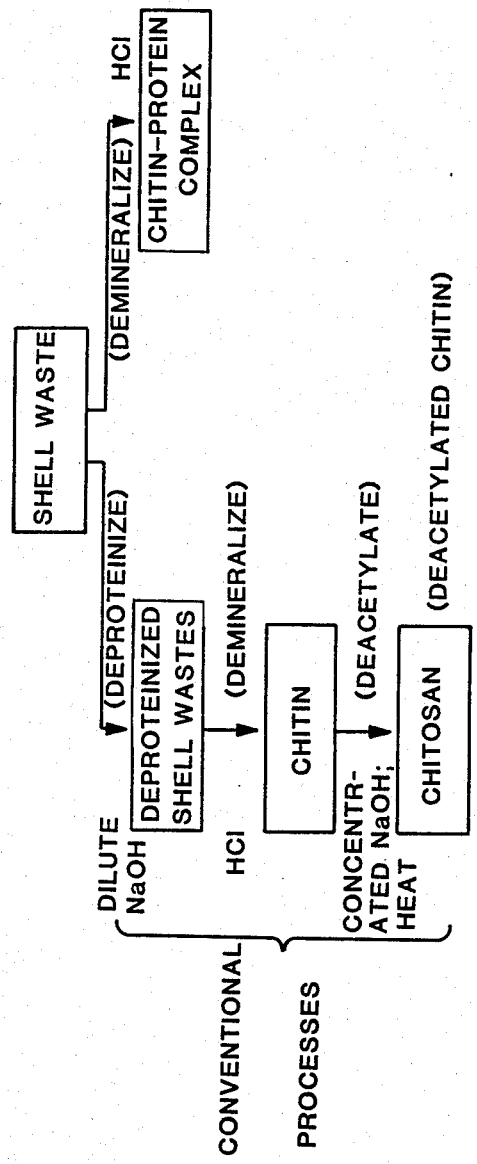
FIG. 3 illustrates conventional processes used to treat shellfish wastes for the production of commercial chitin and chitosan products as they compare with the process disclosed herein. Also shown are the chemical structures of chitin and chitosan.
Figure 3:
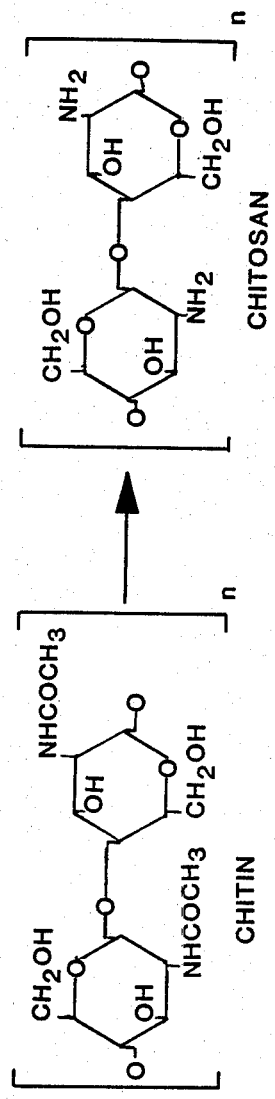
Figure 4A:
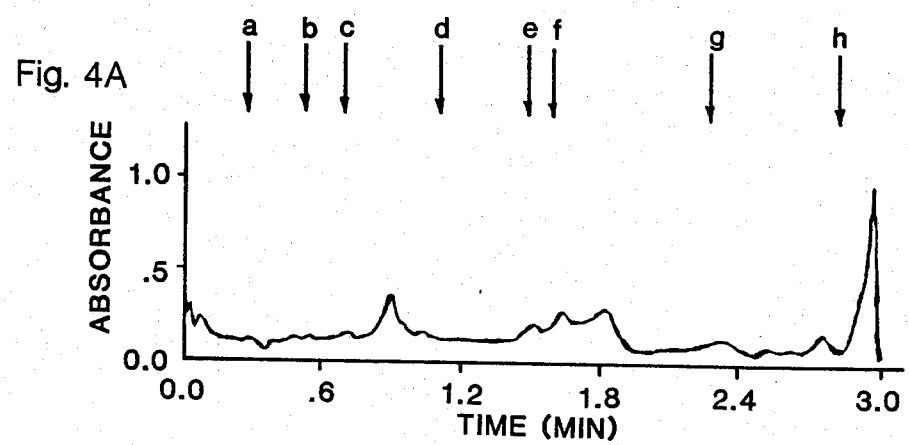
FIG. 4 illustrates the subunit composition of protein components of the chitin-protein complexes prepared in Examples 2, 3 and 4 and of commercial chitin and chitosan preparations.
Figure 4B:
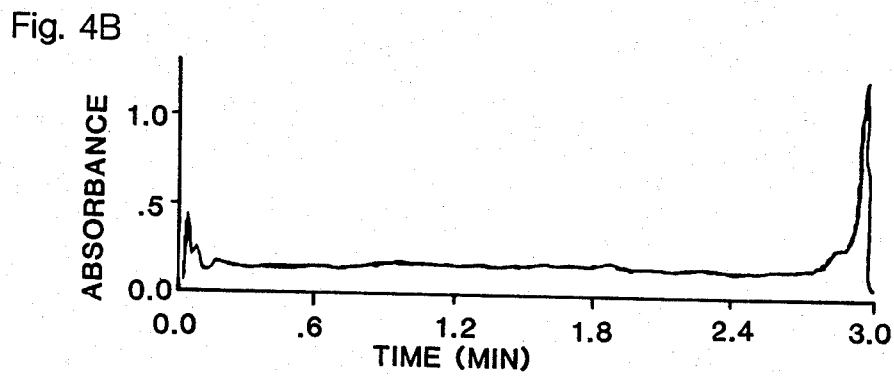
Figure 4C:
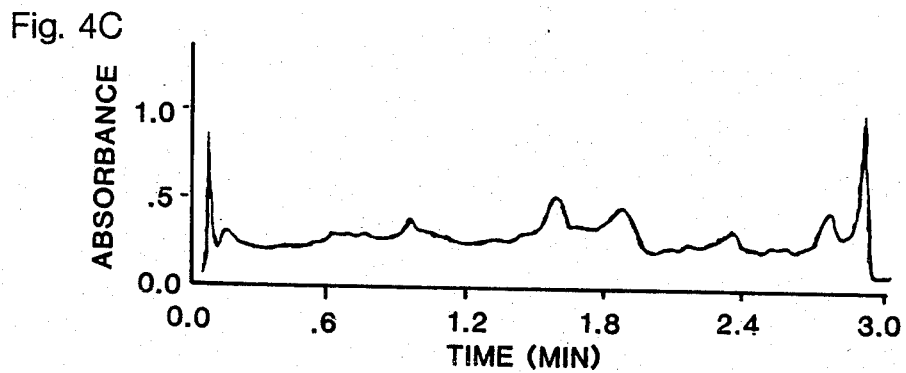
Figure 4D:
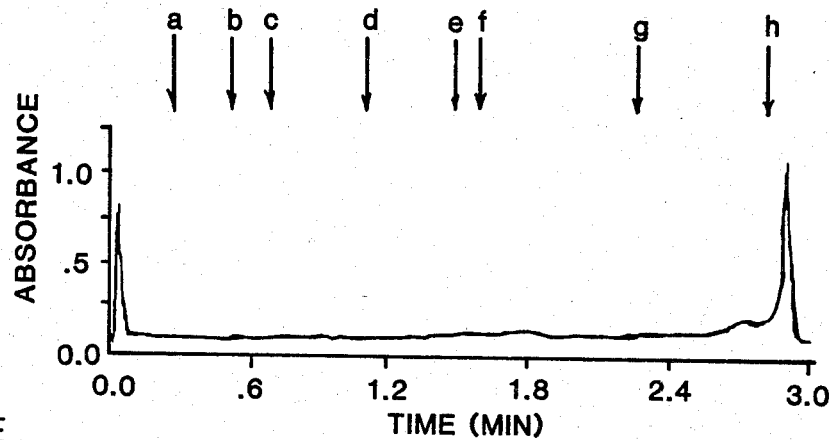
Figure 4E:
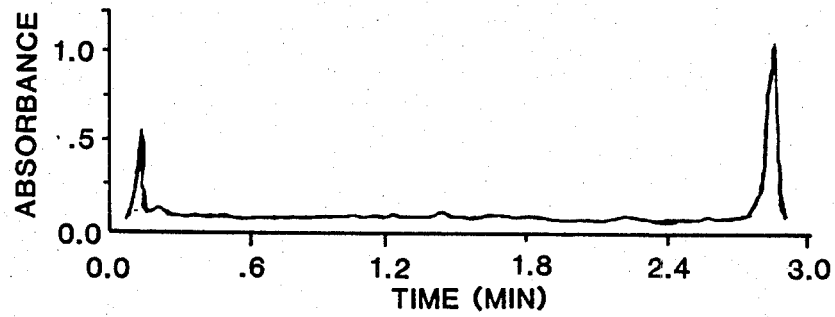
Figure 4F:
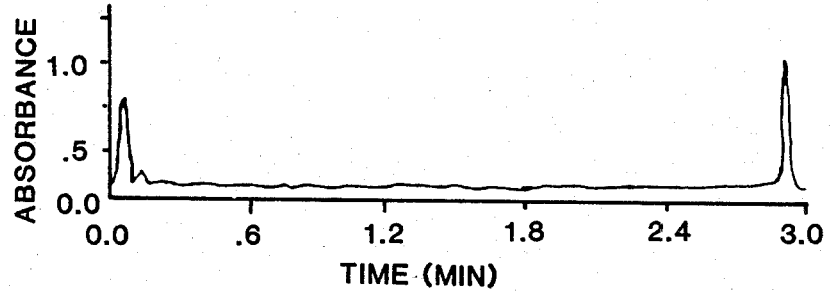
Figure 5A:
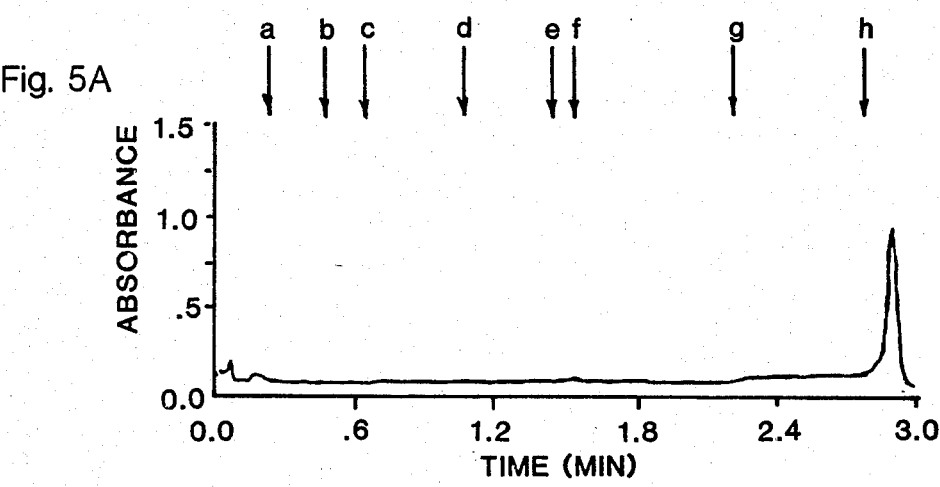
FIG. 5 illustrates the subunit composition of the protein component of the chitin-protein complex obtained by acid treatment of dried fermentor cake from a commercial gibberellin fermentation process as described in Example 5.
Figure 5B:
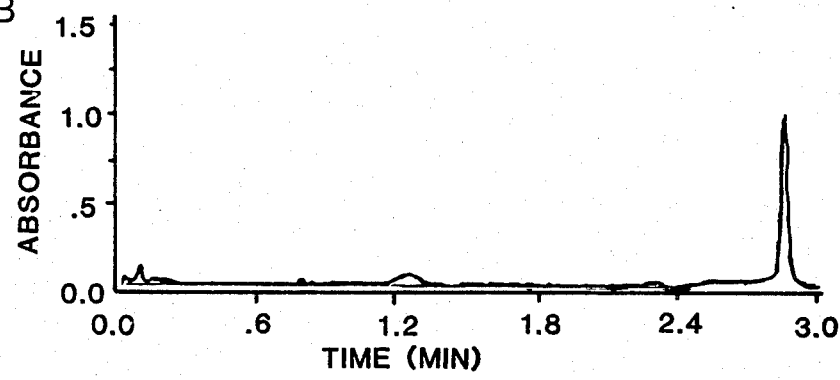
Figure 6:
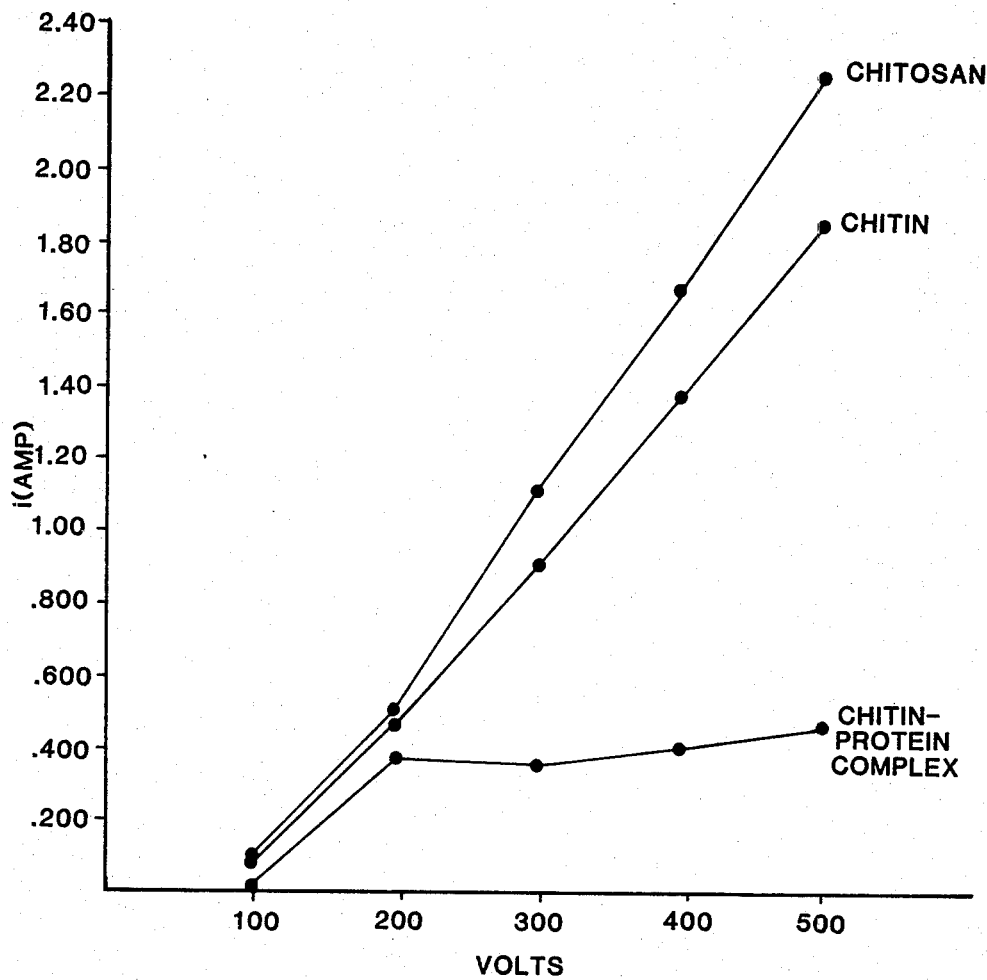
FIG. 6 is a plot of the alternating current (ac) conductivity of chitin, chitosan and the crabshell chitin-protein complex as a function of applied voltage.

The insoluble end-product of the reaction which is of specific interest to this disclosure is a chitin-protein complex which has distinctly different gel electrophoretic properties from the product resulting from demineralization of crabshells by chelating agents such as ethylenediaminetetracetic acid (EDTA) (FIG. 4) and from chitin-protein complexes isolated from fungal residues (FIG 5). The solid-state electrical properties of such chitin-protein material are also distinctly different from those of commercial preparations of chitin and chitosan which are produced by substantially more vigorous subsequent treatments (FIGS. 3 and 6).

After completion of demineralization and protein modification (DM/PM) by mild acid hydrolysis, usually at about 60 minutes after the start of the hydrolysis reaction, the resulting chitin-protein material is washed until neutral (pH 7.0) with water or weak soda ash (Na$_2$CO$_3$) solutions. Effluents from the DM/PM and wash water tanks can be recycled for recovery of low molecular weight peptides, amino acids and calcium chloride brine, or can be simply discharged to an approved waterway or wastewater treatment facility. The resulting chitin-protein complex is then dried in a suitable drier and ground, if desired, to a particle size of less than 0.5 mm. No further treatment, as is required in conventional chitin and chitosan processing operations (FIG. 3), is needed.

The resultant chitin-protein complex (FIGS. 4, 6 and 7) is: (i) insoluble in neutral and in dilute acid solutions but solubilized with significant decomposition of the protein component in concentrated mineral acids; (ii) low in ash content; (iii) high in bound nitrogen content owing to the presence of the protein moiety; and (iv) a naturally occurring, biodegradable material which, when added to nematode cultures in vitro, results in a significant reduction in the number of living organisms (FIGS. 11-13). The product can be produced commercially in better yield and at substantially less cost than can either chitin or chitosan derived from crab, lobster, shrimp or other shellfish processing wastes or from the walls of chitin-containing fungi, molds and yeasts. Morphological changes induced in nematode cultures in in vitro culture media are also distinctly different from those which are seen following exposure of prototypical nematode species to chitin or chitosan (FIG. 11).

Preferred rates for application of the chitin-protein complex of this invention to plant growth media range from 1 to 50 weight percent, generally in admixture with a plant growth medium containing the requisite nutrients. More preferred rates are in the range of 2 to 20 weight percent; the presently most preferred rates are in the range of 5 to 10 weight percent. The optimum amount within this range depends upon a number of variables which are well known to those skilled in the art of plant protection. These variables include but are not limited to disease to be controlled, the type of crop, stage of development of the crop and the interval between applications. Applications within the range given may need to be repeated one or more times at intervals of 1 to 6 months.

The chitin-protein complex of this invention can be applied in a variety of formulations, preferably as granules, pellets, etc.

Powder and dust preparations can be made by blending the active ingredient, with or without surfactant, with finely divided solids such as talcs, natural clays, pyrophyllite, diatomaceous earth; flours such as wheat, redwood, and soya bean; or inorganic substances such as magnesium carbonate, calcium carbonate, calcium phosphate, sodium siliocoaluminate, sulfur and the like. The choice of a particular diluent is based on consideration of the physical and chemical properties required of the product, the chemical and physical properties and concentration of the active ingredient, and the use for which the formulation is intended. The compositions are made by thoroughly blending the active ingredient with the diluent and other additives.

Powdered compositions can be converted to granules by adding a liquid, treating mechanically, and usually drying. Mechanical devices such as granulating pans, mixers and extruders can be used. Compaction devices can be used even without a liquid in the mixture. Water soluble binders, e.g. inorganic salts, urea, lignin sulfonates, methyl cellulose, other water soluble polymers and the like, can be included in these particulate formulations in amounts up to about 25% by weight of the finished granule or pellet. Such materials also aid in disintegration of the pellet and release of the active ingredient under field conditions. Alternatively, a suspension of the active ingredient can be sprayed on the surface of preformed granules of clay, vermiculite, corn cob and the like. Surfactants may also be included in formulations of the latter type.

The compositions of the invention can contain, in addition, to the active ingredient of this invention, conventional insecticides, miticides, bactericides, other nematocides, fungicides or other agricultural chemicals such as fruit set agents, fruit thinning compounds, fertilizer ingredients and the like, so that the compositions can serve useful purposes in addition to its nematocidal activity.

Because of its protein, the chitin-protein complex of this invention contains about 10 percent nitrogen in a slow-release form; it can advantageously be mixed with sources of metabolizable phosphorous and/or potassium to provide a balanced fertilizer. The nitrogen content can be enhanced by the further addition of other nitrogen fertilizer sources which are well known in the art. The presently preferred embodiment of this invention is for use in a potting mixture with soil or a particulate inorganic material such as vermiculite, e.g. for growing greenhouse plants or nursery stock. In one embodiment, Harposporium fungus is added to enhance the nematocidal activity of the chitin-protein complex.

Pathogenic plant nematodes which may be controlled in accordance with the present invention include but are not limited to those set forth in the following table.

TABLE I

| PATHOGENIC PLANT NEMATODES | |
| --- | --- |
| NEMATODE | PLANT HOST |
| *Aphelenchoides besseyi* | Strawberry |
| *Ditylenchus dipsaci* | Root crops |
| *Heterodera rostochiensis* | Potato |
| *Ditylenchus destructor* | Potato |
| *Pratylenchus penetrans* | Tobacco, apple, cherry |
| *Xiphinema americanum* | Grasses, Citrus, Tomato |
| *Meloidogyne hapla* | Potato |
| *Tylenchulus semipenetrans* | Citrus |
| *Ditylenchus myceliophagus* | Mushroom |
| *Tylenchorhynchus claytoni* | Tobacco |
| *Hemicriconemoides chitwoodi* | Camellia |
| *Hemicycliophora arenaria* | Citrus |
| *Paratrichodorus christiei* | Celery |
| *Paratylenchus projectus* | Grass |
| *Dratylenchus zeae* | Corn |
| *Hoplolaimus columbus* | Soybean |
| *Pratylenchus neglectus* | Corn, strawberries, etc. |

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. All temperatures are set forth uncorrected in degrees Celsius; unless otherwise indicated, all pressures are ambient and all parts and percentages are by weight. The values obtained by elemental analysis are within the usual limits of experimental error; all new products gave the expected parent peaks in IR.

EXAMPLE 1

Preparation of Raw Material

Crabmeal processing waste obtained from a commercial supplier was water washed, dried in a hot-air oven at 100° C. for approximately 16 hours and then shredded mechanically to a particle size such that all of the material passed through a No. 25 USA Standard Testing Sieve. The resulting particles had a moisture content of 5-10% and contained approximately 40-50% protein and 30-50% $CaCO_3$ on a dry weight basis. Elemental composition of three representative batches of otherwise untreated raw material feedstock is illustrated in Table II. Protein content was determined by the method of Lowry (which measures tyrosine and peptide bond content). Nitrogen content was determined using combustion analysis based on the Pregl-Dumas method and a Perkin-Elmer model 240B Elemental Analyzer.

TABLE II

Composition of Shellfish Starting Materials

| ELEMENT | UNFRACTIONATED[1] | SIZED[2] | GROUND[3] |
|---|---|---|---|
| Calcium (ug/g) | 92900.0 | 94999.0 | 95900.0 |
| Sodium (ug/g) | 9470.0 | 12000.0 | 10500.0 |
| Magnesium (ug/g) | 4880.0 | 5170.0 | 5030.0 |
| Potassium (ug/g) | 4160.0 | 3390.0 | 4420.0 |
| Strontium (ug/g) | 1070.0 | 1000.0 | 1170.0 |
| Iron (ug/g) | 361.0 | 410.0 | 716.0 |
| Aluminum (ug/g) | 100.0 | 103.0 | 206.0 |
| Barium (ug/g) | 25.5 | 23.5 | 34.6 |
| Boron (ug/g) | 4.5 | 4.5 | 6.6 |
| Cadmium (ug/g) | <0.5 | <0.5 | <0.5 |
| Chromium (ug/g) | 1.0 | 1.5 | 1.6 |
| Cobalt (ug/g) | <1.0 | <1.0 | <3.3 |
| Copper (ug/g) | 27.0 | 25.0 | 36.3 |
| Lead (ug/g) | <2.5 | <2.5 | <8.2 |
| Manganese (ug/g) | 150.0 | 145.0 | 228.0 |
| Molybdenum (ug/g) | <1.0 | <1.0 | <3.3 |
| Zinc (ug/g) | 69.0 | 57.5 | 74.2 |
| Carbon (%) | 29.84 | 34.76 | 34.01 |
| Hydrogen (5) | 3.96 | 4.74 | 5.59 |
| Nitrogen (%) | 5.46 | 6.29 | 7.19 |
| Protein (Lowry) (%) | 32.4 | 43.0 | 41.8 |
| Ash (%) | 45.76 | 36.65 | 37.22 |
| Moisture (%) | 7.41 | 10.47 | 8.11 |

[1] Shredded shellwastes, as received (Batch 118)
[2] Shredded shellwastes, sized through ASTM 40 mesh screen (Batch 118)
[3] Shredded shellwastes, ground to <0.5 mm size (Batch 524)

EXAMPLE 2

Laboratory-Scale Isolation of Crabshell Chitin-Protein Complex by Acid Demineralization The subunit composition was determined by electrophoresis on a 10% polyacrylamide gel containing 0.1% sodium dodecyl sulfate (SDS). Shown are scans of the gels after staining of the proteins with Coomassie Brilliant Blue R. The position indicated by the arrows are the positions of standard molecular weight (given in daltons in parentheses) marker proteins: (a) myosin (200,000), (b) beta-galactosidase (116,500), (c) phosphorylase B (97,400), (d) bovine serum albumin (66,200), (e) ovalbumin (45,000), (f) carbonic anhydrase (31,000), (g) soybean trypsin inhibitor (21,500), and (h) lysozyme (14,400). The samples run were 5 mg of (A) (starting material), (B) starting material after 10 minutes in acid, (C) after 30 minutes, (D) 60 minutes and (E) the final product after acid treatment, washing, and drying.

Four hundred grams of the raw material described in Example 1 were slowly added over a 30 minute period to 2 liters of 1.0N HCl with continuous stirring. The reaction caused rapid demineralization of the $CaCO_3$ phase of the raw material feedstock as evidenced by foaming of the reaction mixture and the release of $CO_2$ gas containing readily detectable amine odors. Approximately 40 mls. concentrated HCl were then added in small aliquots to the reaction mixture (to maintain acidity at approximately pH 1.5) over a period of about 60 minutes, after which no further foaming was observed. The insoluble residue remaining after the demineralization and partial hydrolysis procedure was collected on a No. 270 U.S.A. Standard Testing Sieve and washed with water until both the product and the washings were neutral (pH 7.0). The insoluble product was oven-dried at 100° C. overnight yielding 128 grams of product (32% yield). The dried product was ground in a Wiley Laboratory Mill to a particle size of less than 0.5 mm. for use in all subsequent studies.

EXAMPLE 3

Laboratory-Scale Isolation of Crabshell Chitin-Protein Complex by Treatment with a Chelating Agent Ten grams of the raw material feedstock described in Example 1 were added to 1 liter of 0.1M ethylenediaminetetraacetic acid (EDTA), pH 7.5, and the mixture stirred continuously at 25° C. for 72 hours. The residual insoluble product was collected on a No. 270 U.S.A. Standard Testing Sieve and washed exhaustively with water. The resulting product was oven-dried at 100° C. overnight with recovery of 2.75 g of dry product (27% yield).

EXAMPLE 4

Pilot-Scale Preparation of Crabshell Chitin-Protein Complex

Fifteen kilograms of the raw material feedstock described in Example 1 were slowly added to 100 liters of 1.25N HCl in a 200 liter stainless steel stirred tank reactor. The rate of addition of feedstock was regulated so as to minimize foaming over the course of a 60-minute demineralization and acid hydrolysis reaction. Insoluble product remaining after demineralization and acid hydrolysis was collected on a Sweco ® Vibro-Energy ® separator equipped with a 150-mesh self-cleaning stainless steel screen, washed with water and then 1% $Na_2CO_3$ and, finally, washed with water again to remove all soluble carbonates. The neutral (pH 7.0) product was oven-dried at 100° C. overnight and then ground to a particle size of less than 0.5 mm. prior to use. The elemental compositions of the preparations from Examples 2, 3, and 4 as compared to chitin and chitosan are shown in Table III.

FIG. 4 illustrates the subunit composition of protein components of the chitin-protein complexes prepared in Examples 2, 3, and 4 and of commercial chitin and chitosan preparations as determined by electrophoresis on a 10% polyacrylamide gel containing 0.1% SDS. Shown are scans of Coomassie Brilliant Blue R—stained gels. Samples are 5 mg of (A) untreated crabshell wastes described in Example 1, (B) chitin-protein complex obtained by mild acid hydrolysis described in Example 2, (C) chitin-protein complex prepared by demineralization with ethylenediaminetetraacetic acid (EDTA) described in Example 3, (D) chitin protein complex prepared as in Example 4, (E) chitin obtained commercially, and (F) chitosan obtained commercially.

Arrows indicate positions of migration of molecular weight markers as in FIG. 2.

TABLE III

Composition of Chitin, Chitosan, and Chitin-protein Complex

| ELEMENT | Chitin (Sigma) | Chitin (Bioshell) | Chitosan (Sigma) | Chitosan (Bioshell) | Chitin-protein Complex (Batch 118) | Chitin-protein Complex (Batch 524) | Chitin-protein Complex (Batch SP001) | EDTA-Demineraliz. Wastes |
|---|---|---|---|---|---|---|---|---|
| Calcium (ug/g) | 6780.0 | 237.0 | 16300.0 | 200.0 | 160.0 | 151.0 | 7076.0 | 2150.0 |
| Sodium (ug/g) | 155.0 | 102.0 | 456.0 | 1530.0 | 23.3 | 42.0 | 996.6 | 135.0 |
| Magnesium (ug/g) | 316.0 | 40.6 | 661.0 | 45.9 | 73.5 | 24.3 | 310.0 | 419.0 |
| Potassium (ug/g) | <23.0 | <27.0 | <30.4 | 16.6 | 13.4 | <24.2 | <20.0 | <49.2 |
| Strontium (ug/g) | 118.0 | 1.4 | 254.0 | 5.8 | 2.0 | 1.2 | 92.3 | 4.9 |
| Iron (ug/g) | 2000.0 | 86.7 | 337.0 | 187.0 | 609.0 | 257.0 | 180.6 | 246.0 |
| Aluminum (ug/g) | 46.0 | 20.3 | 45.6 | 16.6 | 184.0 | 42.5 | 51.6 | 52.2 |
| Barium (ug/g) | 2.3 | <1.4 | 1.5 | 0.8 | 1.3 | 3.6 | 4.0 | 86.2 |
| Boron (ug/g) | 2.3 | 1.4 | 1.5 | 0.8 | 1.3 | 1.2 | <2.0 | 2.5 |
| Cadmium (ug/g) | <1.1 | <1.4 | <1.5 | <0.8 | <0.6 | <1.2 | <1.0 | 2.5 |
| Chromium (ug/g) | 5.7 | 1.4 | 6.0 | 18.3 | 1.3 | 1.2 | 1.0 | 2.5 |
| Cobalt (ug/g) | <2.3 | 62.7 | <3.0 | <1.6 | <1.3 | <2.4 | <2.0 | 2.4 |
| Copper (ug/g) | 4.6 | 2.7 | 3.0 | 1.6 | 24.0 | 26.7 | 26.6 | <4.9 |
| Lead (ug/g) | <5.7 | <6.7 | <7.6 | <4.1 | <3.3 | <6.0 | <5.0 | 24.6 |
| Manganese (ug/g) | 35.6 | <1.4 | 12.2 | 3.3 | 4.6 | 1.2 | 22.6 | <12.3 |
| Molybdenum (ug/g) | <2.3 | <2.7 | <3.0 | <1.6 | <1.3 | 2.4 | <2.0 | 2.5 |
| Zinc (ug/g) | 100.0 | 2.7 | 35.0 | 2.5 | 3.3 | 2.4 | 16.0 | <4.9 |
| Carbon (%) | 45.36 | 46.98 | 42.16 | 45.13 | 53.27 | 51.54 | 48.10 | 7.4 |
| Hydrogen (%) | 6.41 | 6.86 | 6.74 | 7.09 | 7.45 | 7.50 | 7.00 | 7.15 |
| Nitrogen (%) | 6.61 | 6.92 | 7.75 | 8.18 | 11.12 | 10.92 | 9.99 | 11.11 |
| Protein (Lowry) (%) | <1.0 | <1.0 | <1.0 | <1.0 | 74.4 | 76.9 | 54.4 | 51.0 |
| Ash (%) | 2.32 | 0.08 | 1.61 | n.d. | 3.36 | 3.00 | 3.00 | n.d.[a] |
| Moisture (%) | 7.06 | 6.33 | 9.49 | n.d. | 3.74 | 4.78 | 3.50 | n.d.[a] |

[a] n.d. - not determined

EXAMPLE 5

Laboratory-Scale Isolation of Chitin-Protein Complex From Dried Fungal Biomass Dried fermentor cake obtained from a commercial gibberellin fermentation process was used as a raw material feedstock in place of the crabshell raw material feedstock described in Examples 1 through 4. Two hundred grams of dried fungal biomass were added to 1,000 ml. of 1.0N HCl and the mixture stirred continuously for a period of one hour. There was no appreciable release of gas nor any significant neutralization of the HCl solution during the course of the reaction. Residual insoluble material was collected by centrifugation for 10 minutes at 10,000 rpm in a Sorvall GSA rotor at 4° C. The pellet was resuspended in water and centrifuged again as described above. This procedure was repeated four times, by which point the residual insoluble biomass material and the washings were neutral (pH 7.0). Insoluble material remaining after the fifth centrifugation procedure was oven-dried overnight at 100° C. with recovery of 88 grams of solid material (44% yield). This material was ground in a Wiley Laboratory Mill to a particle size of less than 0.5 mm. prior to use. Its composition is shown in Table IV:

FIG. 5 illustrates the subunit composition of the protein component of the chitin-protein complex obtained by acid treatment of dried fermentor cake from a commercial gibberellin fermentation process as described in Example 5. Scan (A) represents the acid-treated material and scan (B) represents untreated fungal fermentor cake. Arrows indicate the positions of migration of molecular weight markers as in FIG. 2.

TABLE IV

Composition of Fungal Preparations

| ELEMENT | Fungal Fermentor Cake | Acid-Treated Fungal Fermentor Cake |
|---|---|---|
| Calcium (ug/g) | 766.0 | 174.0 |
| Sodium (ug/g) | 102.0 | 160.0 |
| Magnesium (ug/g) | 1000.0 | 23.5 |
| Potassium (ug/g) | 8270.0 | 132.0 |
| Strontium (ug/g) | 3.2 | 1.9 |
| Iron (ug/g) | 106.0 | 237.0 |
| Aluminum (ug/g) | 26.9 | 28.1 |
| Barium (ug/g) | 1.1 | <0.9 |
| Boron (ug/g) | 2.1 | 3.7 |
| Cadmium (ug/g) | <1.0 | <0.9 |
| Chromium (ug/g) | 1.0 | <1.9 |
| Cobalt (ug/g) | <2.1 | 1.9 |
| Copper (ug/g) | 8.6 | 1.9 |
| Lead (ug/g) | <5.4 | <4.7 |
| Manganese (ug/g) | 8.6 | 2.8 |
| Molybdenum (ug/g) | <2.1 | <1.9 |
| Zinc (ug/g) | 22.7 | 1.9 |
| Carbon (%) | 52.74 | 54.41 |
| Hydrogen (%) | 7.07 | 7.61 |
| Nitrogen (%) | 6.73 | 6.20 |
| Protein (lowry) (%) | 31.46 | 29.32 |
| Ash (%) | 4.96 | 30.75 |
| Moisture (%) | 4.04 | 5.33 |

EXAMPLE 6

Characterization of the Chitin/Protein Complexes

Figure 7A:
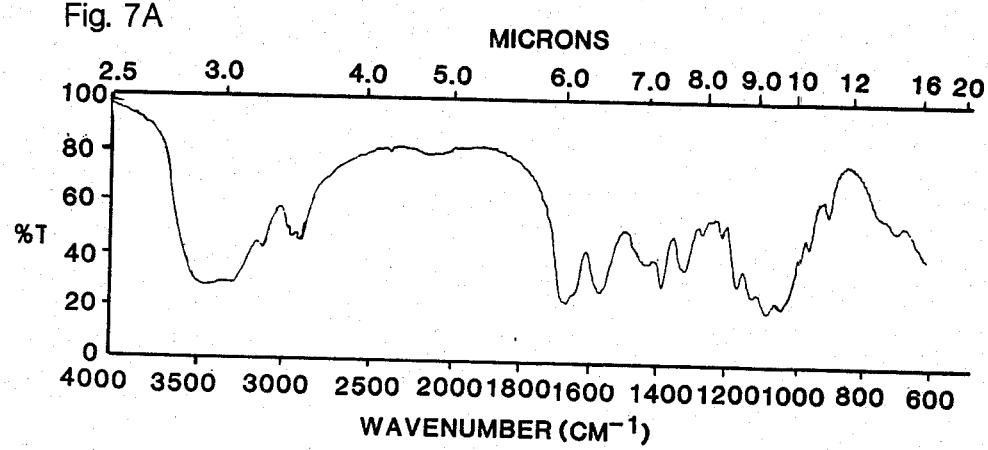
FIG. 7 demonstrates the infrared spectra of (A) chitin, (B) the chitin-protein complex of this invention, and (C) chitosan.
Figure 7B:
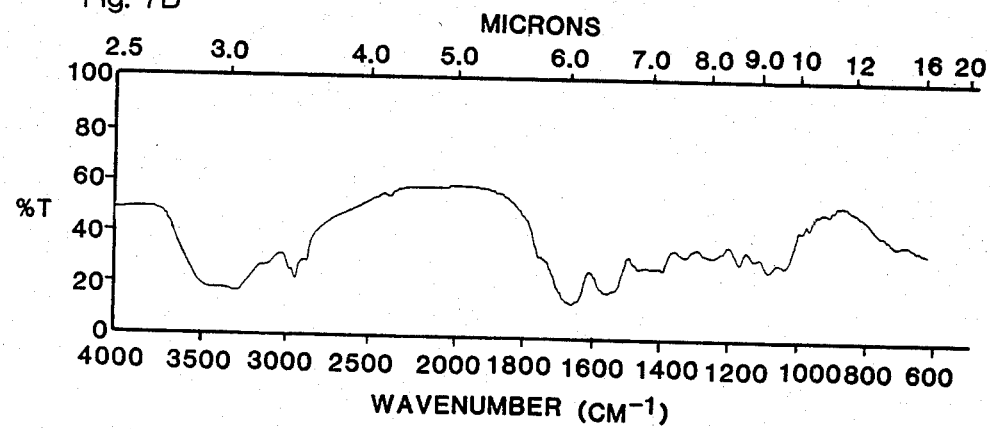
Figure 7C:
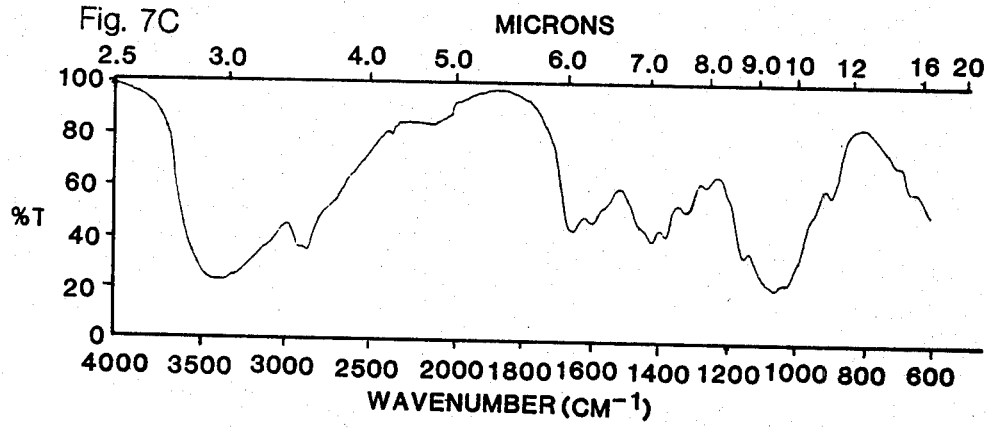
Figure 8A:
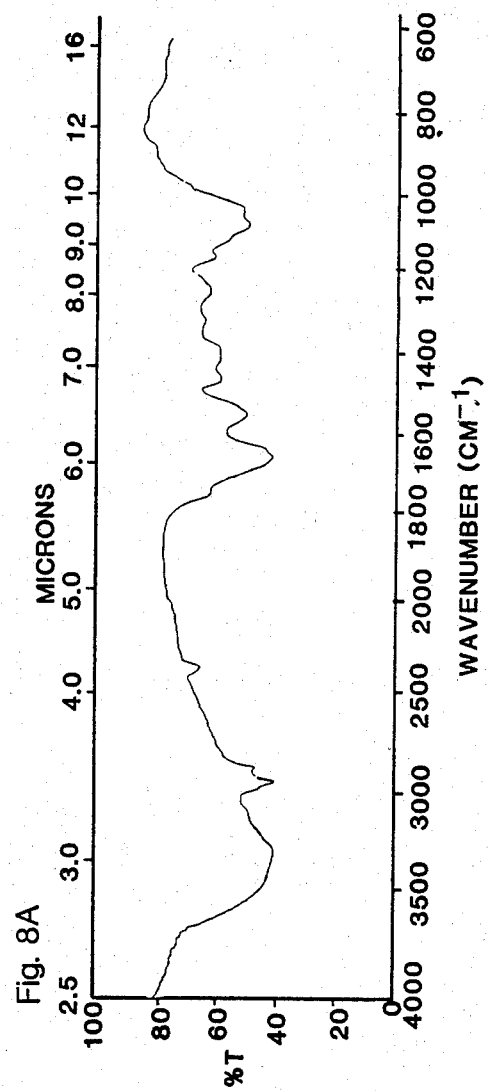
FIG. 8 illustrates the infrared spectra of (A) untreated fungal fermentation cake and (B) an acid-treated fungal fermentation cake product of this invention.
Figure 8B:
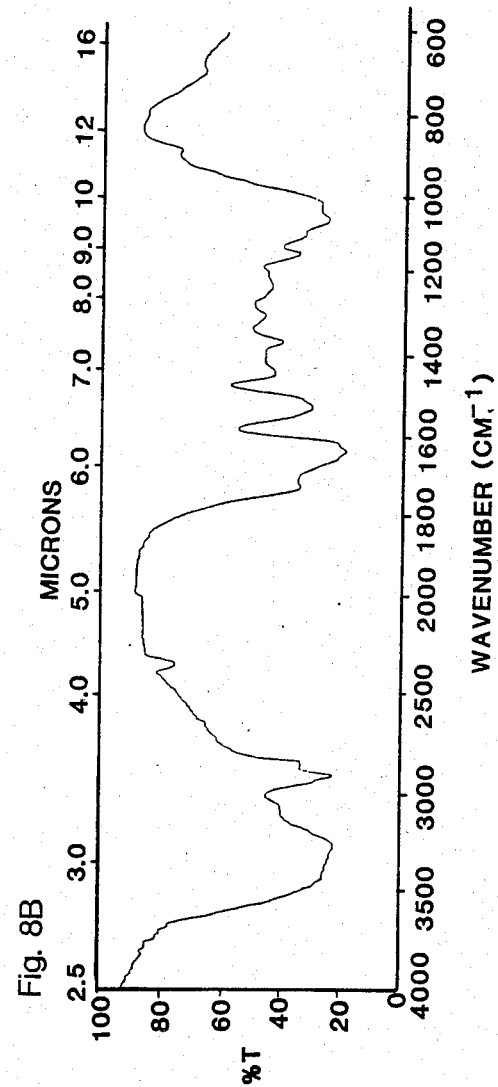
Figure 9A:
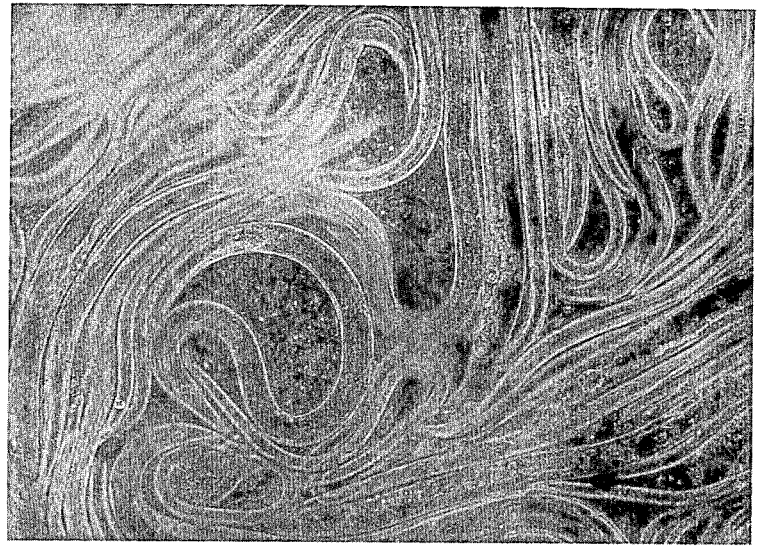
FIG. 9 demonstrates the light microscopic appearance of *Panagrellus spp.* nematodes in control culture media (A and B) at 16–20 days after innoculation and the appearance of nematodes at 16–20 days after innoculation in test media containing chitin the chitin-protein complex (C and D) of this invention.
Figure 9B:
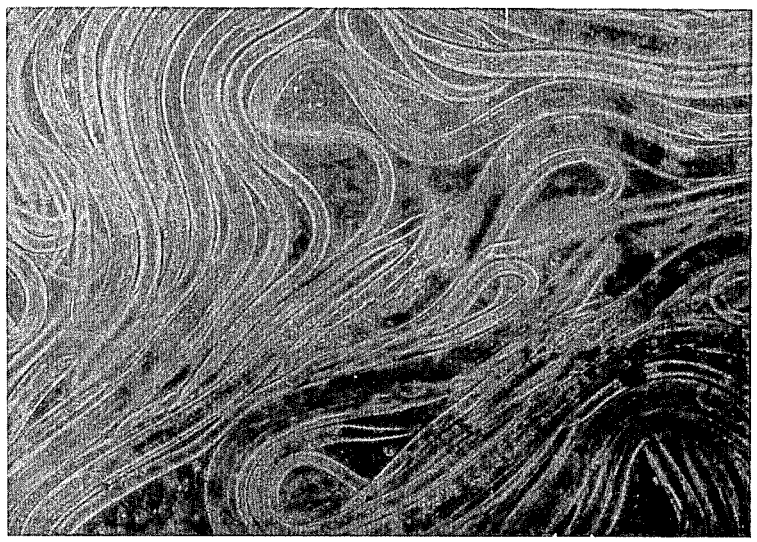
Figure 9C:
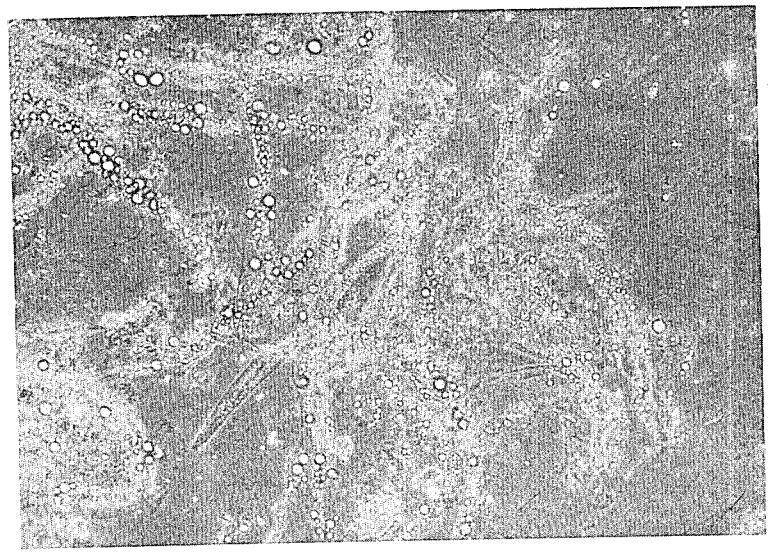
Figure 9D:
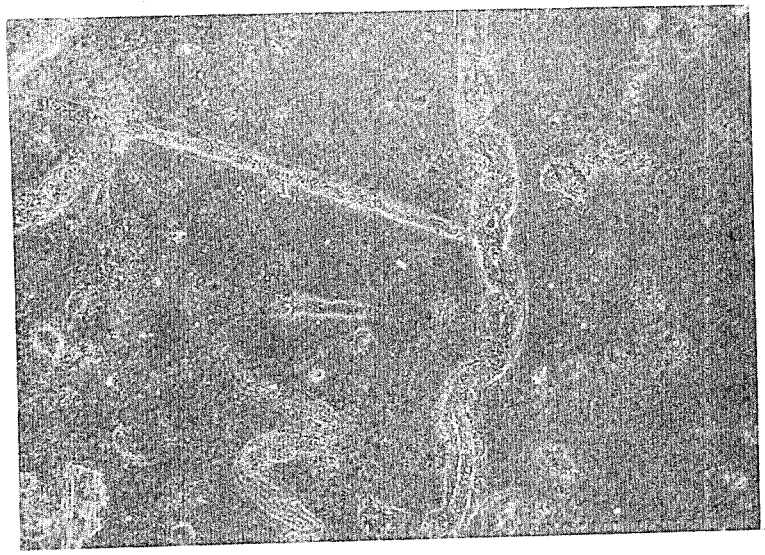

Samples of crabshell raw material and each of the test materials (particle size less than 0.5 mm.) were analyzed for carbon, hydrogen, nitrogen, ash and metal contents; for total protein and amino acid content (Tables II, III, and IV); for solid-state electric properties (FIG. 6); and by infrared spectroscopy (FIGS. 7–8). Elemental composition was determined using Inductively Coupled Plasma Emission Spectroscopy (ICP) for metal analysis and a Perkin-Elmer 240B Elemental Analyzer for carbon, hydrogen and nitrogen analysis. A Perkin-Elmer Model 1320 Infrared Spectrophotometer was used to measure infrared spectra of all materials. Total protein content was determined by extraction of each of the materials with 1.0N NaOH for 48 hours at 25° C., followed by determination of the protein content in the solution by the Lowry method. For amino acid analysis, samples were hydrolyzed in vacuo in 6N HCl for 24 hours at 110° C. and the amino acids were measured after separation by high performance liquid chromatography (HPLC) according to standard methods such as those recently reviewed by M. W. Dong and J. C. DeCesare in Liq. Chrom. 1, 222–228 (1983). Solid-state electrical properties were measured by an electrical testing laboratory using standard techniques. The amino acid compositions are shown in Table V.

EXAMPLE 7

Characterization of the Protein Component of the Chitin-Protein Complex

During the acid-demineralization of crab shell wastes, the amount of high molecular weight protein extractable by sodium dodecyl sulfate decreases (FIG. 2). The total amount of protein, however, remains nearly constant (Table III) and the protein can only be removed by extended alkaline hydrolysis, indicating that in the acid treatment the protein is either made more detergent insoluble, is partially degraded, is covalently linked to the chitin matrix, or a combination of these possibilities. The amino acid analysis of the starting material and of the chitin-protein complex (Table V) demonstrates no significant change in amino acid composition during mild acid hydrolysis, indicating that the relative amounts of the proteins present in the starting materials and in the final product are not very different. As seen in FIG. 4, there is no significant amount of protein in commercial preparations of chitin or chitosan. The chitin-protein complex prepared using EDTA to demineralize the material, on the other hand, contains a significant amount of protein which has not been modified.

TABLE V

Amino Acid Composition of Crab Shell Wastes, Acid-demineralized Crab Shell Wastes, and Acid EDTA-demineralized Crab Shell Wastes

| Amino Acid[a] | Starting Material | Chitin/Protein Complex | | EDTA-demineralized Crab Shell Wastes |
|---|---|---|---|---|
| | | Batch 524 | Batch 118 | |
| Asp[b] | 10.8 | 8.3 | 10.5 | 13.3 |
| Thr | 3.6 | 8.6 | 4.5 | 13.6[c] |
| Ser | 4.9 | 5.5 | 4.8 | |
| Glu[b] | 9.9 | 13.4 | 12.9 | 12.2 |
| Gly | 5.0 | 3.9 | 3.9 | 4.2 |
| Ala | 5.6 | 5.3 | 5.4 | 5.5 |
| Val | 3.6 | 5.2 | 5.9 | 6.0 |
| Met | 1.8 | 3.3 | 3.5 | 3.1 |
| Ile | 4.4 | 5.4 | 5.5 | 5.1 |
| Leu | 10.5 | 8.5 | 9.0 | 7.4 |
| Tyr | 4.9 | 5.9 | 5.7 | 5.9 |
| Phe | 10.8 | 9.3 | 9.8 | 5.9 |
| Lys | 12.5 | 7.3 | 8.3 | 7.5 |
| His | 3.0 | 2.9 | 3.2 | 3.0 |
| Arg | 8.8 | 7.1 | 7.0 | 7.2 |

[a]Cysteine, proline, and tryptophan were not determined.
[b]Asparagine and glutamine are included with Asp and Glu, respectively.
[c]Ser + Thr

EXAMPLE 8

Characterization of the Chitin Component of the Chitin-Protein Complex

The chitin-protein complex was analyzed by infrared spectroscopy and compared with commercially available chitin and chitosan (FIG. 7). The chitin-protein complex gives a spectrum very similar to that of chitin with the exception of an extra absorption band at 1738 cm$^{-1}$, possibly due to the protein component. The absorption band at 1550 cm$^{-1}$ in chitin and in the chitin-protein complex, which is shifted in chitosan, appears related to acetylation of the amino groups in chitin. The relative intensities of this band in chitin and the chitin-protein complex indicate that there is very little deacetylation of chitin during preparation of the chitin-protein complex.

Infrared spectra of the fungal preparations were measured (FIG. 8). The spectra are very similar to that of chitin, and the spectra of both preparations (untreated, acid) are similar, indicating very little change in the form of the chitin in the materials.

The chitin-protein complex has solubility properties similar to those of chitin, i.e. it is insoluble in most ordinary solvents. The protein portion can be partially solubilized by detergents and other protein solvents such as urea or guanidinium salts, or by treatment with alkali. Chitosan, on the other hand, is soluble in dilute organic acids (1% acetic, lactic, propionic, and formic acids). All of the materials are soluble in concentrated mineral acids, but significant degradation occurs.

EXAMPLE 9

Preparation of the Nematocide Test System

Panagrellus, a saprophytic nematode obtained from Dr. Julius Feldmesser at the U.S. Department of Agriculture Plant Protection Institute, Beltsville, Md., was cultured in a commercially available oatmeal cereal (Gerber Products Co., Fremont, Mich.). The nematodes were cultured in 60×22 mm sterile plastic petri dishes containing 6 grams of autoclaved oatmeal cereal and 20 ml of sterile distilled water. The dishes were inoculated with approximately 2000 nematodes suspended in 2 ml of sterile distilled water. The cultures were then incubated at 30° C. for 21 days. Control cultures contained only oatmeal cereal, distilled water, and nematodes in the above proportions. Materials to be tested for nematocidal activity were autoclaved and added to the individual culture dishes at the level of 0.2 grams per dish. Both control and test cultures were set up in series of five samples.

EXAMPLE 10

Measurement of Nematocidal Activity

Cultures of Panagrellus were prepared and observed according to the test system presented in Example 9. Observations were made beginning day 6 and continued through day 21, or until the cultures died.

Microscopic observations were made using the wet mount slide technique on 0.01 ml samples withdrawn from the active surface zone of the cultures where Panagrellus existed. An average of the numbers obtained by counting the samples withdrawn from each of the culture dishes in the series was used to determine the relative population. Counts were made beginning on the sixth and continuing through to the 21st day. Averaged results are shown in Table VI, where a significant reduction in numbers of nematodes in cultures treated with the chitin-protein complex of this invention can be seen.

TABLE VI

Effect of Various Preparations on the Number of Living Nematodes in Cultures

| | Number of Living Organisms[a] |
|---|---|
| Control | 1,300–1,500 |
| Chitin[b] | 600–700 |
| Chitosan[b] | 900–1,000 |
| Chitin-Protein Complex[b] | 0–400 |

[a] - Motile organisms counted in a 0.01 ml sample taken from the surface of the test plates
[b] - Additions were present at 3% (w/w)

The most significant and reproducible reduction in the total number of organisms was seen at day 17 and later. While there was a reduction in the population in the cultures treated with the chitin-protein complex, chitin, and chitosan, the most significant reduction was observed with the chitin-protein complex of this invention which also offers significant economic advantages over the use of the more highly purified preparations of chitin and chitosan. The fungal fermentation cake is not presently available in quantities sufficient to consider it as a practical raw material for this process.

Figure 10A:
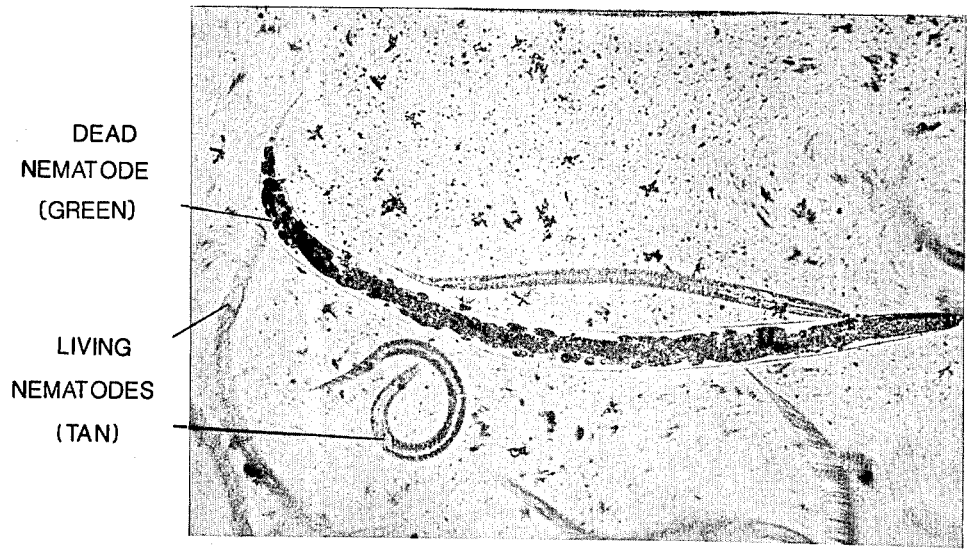
FIG. 10 shows living and dead nematodes stained with Brilliant Green.
Figure 10B:
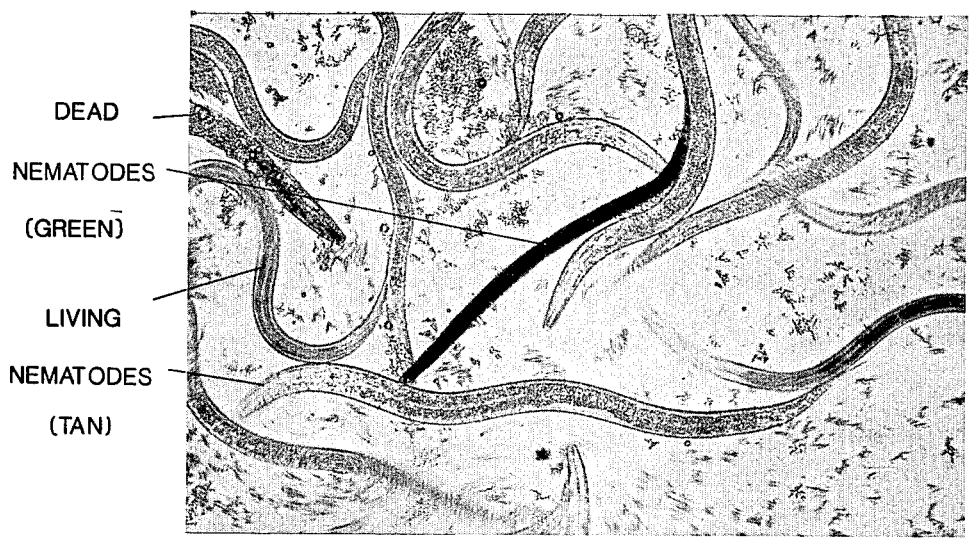

Nematocidal activity in nematode test populations, as documented by photos shown in FIG. 9 (A–D), included a variety of events evident in all stages of development. Loss of motility, a standard determination of death in nematodes, was reinforced by avital staining with Brilliant Green, (C.I. 42040) and Brilliant Cresyl Blue (C.I. 51010). Staining was performed by adding a drop of a 0.05% aqueous solution to a preparation of the organisms on a microscope slide. Within three minutes, there was a clear distinction between living and dead organisms (FIG. 10). The living organisms were not stained, while the dye was taken up by the dead organisms. Cuticle disruption was evident as shown in FIG. 9. Unique to the chitin-protein complex treated cultures was the appearance of large vacuoles, indicating premature senescence, in nematodes of all stages as early as day 13. This appearance of vacuoles was not observed in cultures treated with any of the other materials.

EXAMPLE 11

Nematostatic and Nematocidal Activity of Chitin-Protein Complex in Cultures with Soil Soil chosen randomly from agricultural fields was mixed with the chitin-protein complex at ratios of 0.05, 0.025 and 0.01 complex/soil (wt/wt). Identical portions of these mixtures were then spread on water agar plates and incubated at room temperature. During this time the endogenous population of saprophytic nematodes developed. Several species were seen, predominantly *Panagrellus sp.* and *Rhabditis sp.* The numbers of living and dead organisms in the cultures were counted. As shown in Table VII, the maximum killing was obtained with 5% chitin-protein complex. Control experiments with chitin and chitosan showed substantially less efficient killing of only 33% and 49%, respectively, at day 33. Microscopic examination showed the nematophagous fungus Harposporium to be present in the cultures where maximum killing occurred. This may reflect the mode of action of the chitin-protein complex, which may stimulate nematophagous fungi.

The following table shows the nematocidal activity observed in triplicate experiments, three plates per sample, of the chitin-protein complex on the growth of nematodes cultured in the presence of soil:

TABLE VII

In Vitro Soil Activity
Percentages of dead organisms on test plates:

| | 30 days | 45 days | 60 days |
|---|---|---|---|
| Control | 16% | 16% | 19% |
| 1% chitin-protein complex | 52% | 53% | 91% |
| 2.5% chitin-protein complex | 49.7% | 52% | 77% |
| 5% chitin-protein complex | 93.6% | 96% | 80.7% |

The preceding examples can be repeated with similar success by substituting the generically or specifically described reactants and/or operating conditions of this invention for those specifically used in the examples. From the foregoing description, one skilled in the art to which this invention pertains can easily ascertain the essential characteristics thereof and, without departing from the spirit and scope of the present invention, can make various changes and modifications to adapt it to various usages and conditions.

INDUSTRIAL APPLICABILITY

As can be seen from the preceding disclosure, the present invention is industrially useful in converting chitin-containing bilogical waste material into product having nematostatic and nematocidal properties useful in horticultural and agricultural applications.

What is claimed is:

1. A composition of matter comprising a nematocidally active chitin-protein complex derived from crustacean shell waste material and consisting essentially of a water-insoluble demineralized chitin component complexed with a water-insoluble protein component, said complex being essentially free of low molecular weight peptides, amino acids, and calcium chloride brine formed by acid hydrolysis of such waste material, said complex characterized by:

(a) a Lowry protein content of at least about 50% by weight, an ash content of not more than about 15% by weight, and a moisture content of less than about 10% by weight, based on the total composition;

(b) having solubility properties similar to those of chitin in being insoluble in neutral dilute acid solutions but solubilized with significant decomposition of the protein component in concentrated mineral salts;

(c) having an IR spectrum similar to that of chitin but with a characteristic extra adsorption band at 1738 cm$^{-1}$;

(d) the water-insoluble, demineralized chitin component having an acetyl content substantially identical to that of chitin as shown by a characteristic infrared spectrum adsorption band at 1550 cm$^{-1}$, but which is substantially free of carbonates and contains not more than about 15% of the ash content of chitin;

(e) the water-insoluble protein component having an amino acid composition substantially identical to that of untreated crustacean shell waste material, a molecular weight primarily in the range of 10 to 50 kdal as determined by sodium dodecyl sulfate gel electrophoresis, and being essentially insoluble in common protein solvents; and (f) said complex being in the form of dry particles having a diameter of less than about 0.5 mm.

2. A composition according to claim 1, having a Lowry protein content of at least about 70% by weight, an ash content of not more than about 5% by weight, and a moisture content of less than about 5% by weight, based on the total composition.

3. A composition according to claim 1, in the form of a pulverulent solid.

4. A composition of matter comprising a plant growth medium in admixture with a nematocidally effective amount of the chitin-protein complex according to claim 1.

5. A composition according to claim 4, wherein the plant growth medium is soil.

6. A composition according to claim 5, wherein the plant growth medium is a plant potting soil suitable for growing nursery stock.

7. A composition according to claim 6, wherein the plant growth medium is planted with a living plant susceptible to nematode infection.

8. A composition according to claim 4, wherein the plant growth medium is a particulate inorganic material.

9. A composition according to claim 8, wherein the plant growth medium is an expanded mica.

10. A composition according to claim 8, wherein the plant growth medium is planted with a living plant susceptible to nematode infection.

11. A composition according to claim 8, further comprising Harposporium fungus in an amount effective to enhance the nemtocidal activity of said chitin-protein complex.

12. A method for inhibiting the growth of saprophytic nematodes in a plant growth medium capable of supporting such growth, which comprises admixing at least a nematostatically effective amount of the chitin-protein complex according to claim 1 with said plant growth medium to inhibit the growth of said nematodes.

13. A method according to claim 12, wherein the plant growth medium is soil.

14. A method according to claim 12, wherein the plant growth medium is a particulate inorganic material.

15. A method according to claim 12, wherein the plant growth medium is suitable for growing nursery stock.

16. A method according to claim 12, wherein a nematocidally effective amount of the chitin-protein complex is admixed with the plant growth medium.

17. A method according to claim 16, wherein the nematocidally effective amount is at least about 5 percent by weight of the plant growth medium.

18. A nematocidal composition comprising a nematocidally effective amount of the chitin-protein complex according to claim 1 in admixture with a horticulturally acceptable carrier material.

19. A composition according to claim 18 in the form of a pulverulent solid composition.

20. A composition according to claim 18 wherein the carrier material includes a soil conditioning agent.

* * * * *